(12) United States Patent
Morman et al.

(10) Patent No.: US 6,811,865 B2
(45) Date of Patent: Nov. 2, 2004

(54) FILM HAVING HIGH BREATHABILITY INDUCED BY LOW CROSS-DIRECTIONAL STRETCH

(75) Inventors: Michael Tod Morman, Alpharetta, GA (US); Patricia Hsiaoyin Hwang, Alpharetta, GA (US); Audrie Tomoko Ono, Atlanta, GA (US); Howard Martin Welch, Woodstock, GA (US); Charles John Morell, Roswell, GA (US); Faris Ohan, Knoxville, TN (US); Prasad Shrikrishna Potnis, Duluth, GA (US); Michael Allen Daley, Alpharette, GA (US); Sjon-Paul Lee Conyer, Roswell, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 10/685,805

(22) Filed: Oct. 15, 2003

(65) Prior Publication Data

US 2004/0091752 A1 May 13, 2004

Related U.S. Application Data

(62) Division of application No. 09/751,414, filed on Dec. 28, 2000.
(60) Provisional application No. 60/201,830, filed on May 3, 2000.

(51) Int. Cl.$^7$ ................................................ B32B 3/26
(52) U.S. Cl. ................................ 428/317.9; 428/318.4; 428/304.4; 428/515; 428/523; 428/910; 525/240; 524/427
(58) Field of Search ......................... 428/304.4, 317.9, 428/318.4, 515, 523, 910; 524/427; 525/240

(56) References Cited

U.S. PATENT DOCUMENTS

| | | | |
|---|---|---|---|
| 3,338,992 A | 8/1967 | Kinney | 264/24 |
| 3,341,394 A | 9/1967 | Kinney | 161/72 |
| 3,502,538 A | 3/1970 | Petersen | 161/150 |

(List continued on next page.)

FOREIGN PATENT DOCUMENTS

| | | |
|---|---|---|
| EP | 256717 | 2/1988 |
| EP | 283 200 | 9/1988 |
| EP | 309 073 | 3/1989 |
| JP | 1266806 | 10/1989 |
| JP | 7207052 | 8/1995 |
| JP | 9124814 | 5/1997 |
| JP | 10249945 | 9/1998 |
| JP | 11192670 | 7/1999 |
| WO | 98/04409 | 2/1998 |
| WO | 98/05501 | 2/1998 |
| WO | 98/28135 | 7/1998 |
| WO | 98/29503 | 7/1998 |
| WO | 99/33651 | 7/1999 |
| WO | 99/33654 | 7/1999 |
| WO | 00/29199 | 5/2000 |
| WO | 01/23180 | 4/2001 |

*Primary Examiner*—D. Lawrence Tarazano
(74) *Attorney, Agent, or Firm*—Pauley Petersen & Erickson

(57) ABSTRACT

A breathable, substantially liquid impermeable film and laminate are provided for use in a wide variety of personal care garments and protective garments. The film, and laminate containing the film, are extendible in a cross-direction to a stretched width which is at least 25% greater than an original, unstretched width. The film and laminate have a first water vapor transmission rate of at least about 500 grams/m$^2$-24 hours coinciding with the unstretched width. The film and laminate have a much higher second water vapor transmission rate which is at least about 225% of the first water vapor transmission rate, and not less than about 4000 grams/m$^2$-24 hours, coinciding with a stretched width that is only 25% greater than the stretched width.

30 Claims, 3 Drawing Sheets

U.S. PATENT DOCUMENTS

| | | | |
|---|---|---|---|
| 3,502,763 A | 3/1970 | Hartmann | 264/210 |
| 3,542,615 A | 11/1970 | Dobo et al. | 156/181 |
| 3,679,538 A | 7/1972 | Druin et al. | |
| 3,692,618 A | 9/1972 | Dorscher et al. | 161/72 |
| 3,770,537 A | 11/1973 | Elton | |
| 3,802,817 A | 4/1974 | Matsuki et al. | 425/66 |
| 3,843,761 A | 10/1974 | Bierrenbaum et al. | |
| 3,844,865 A | 10/1974 | Elton et al. | |
| 3,849,241 A | 11/1974 | Butin et al. | 161/169 |
| 3,852,224 A | 12/1974 | Bridgeford | |
| 3,870,593 A | 3/1975 | Elton et al. | |
| 3,932,682 A | 1/1976 | Loft et al. | |
| 4,110,392 A | 8/1978 | Yamazaki | |
| 4,187,390 A | 2/1980 | Gore | |
| 4,257,997 A | 3/1981 | Soehngen et al. | |
| 4,340,563 A | 7/1982 | Appel et al. | 264/518 |
| 4,384,023 A | 5/1983 | Okamura et al. | |
| 4,386,129 A | 5/1983 | Jacoby | |
| 4,539,256 A | 9/1985 | Shipman | |
| 4,707,314 A | 11/1987 | Kawahigashi et al. | |
| 4,815,714 A | 3/1989 | Douglas | |
| 4,832,886 A | 5/1989 | Douglas | |
| 4,919,992 A | 4/1990 | Blundell et al. | |
| 4,965,122 A | 10/1990 | Morman | 428/225 |
| 4,975,469 A | 12/1990 | Jacoby et al. | |
| 5,008,296 A | 4/1991 | Antoon, Jr. et al. | |
| 5,173,235 A | 12/1992 | Kamei et al. | |
| 5,238,636 A | 8/1993 | Furukawa et al. | |
| 5,271,839 A | 12/1993 | Moya et al. | |
| 5,358,678 A | 10/1994 | Nakamura et al. | |
| 5,458,951 A | 10/1995 | Kagawa | |
| 5,498,335 A | 3/1996 | Moya | |
| 5,510,176 A | 4/1996 | Nakamura et al. | |
| 5,576,374 A * | 11/1996 | Betso et al. | 524/451 |
| 5,648,107 A | 7/1997 | Kagawa et al. | |
| 5,800,758 A | 9/1998 | Topolkaraev et al. | |
| 5,883,028 A | 3/1999 | Morman et al. | |
| 5,910,136 A | 6/1999 | Hetzler et al. | |
| 5,914,184 A | 6/1999 | Morman | |
| 5,932,497 A | 8/1999 | Morman et al. | 442/286 |
| 5,938,874 A | 8/1999 | Palomo et al. | |
| 5,955,187 A | 9/1999 | McCormack et al. | |
| 5,968,643 A | 10/1999 | Topolkaraev et al. | |
| 5,993,589 A | 11/1999 | Morman | |
| 6,002,064 A | 12/1999 | Kobylivker et al. | 604/367 |
| 6,013,151 A | 1/2000 | Wu et al. | |
| 6,015,764 A | 1/2000 | McCormack et al. | |
| 6,072,005 A | 6/2000 | Kobyl ivker et al. | |
| 6,096,014 A | 8/2000 | Haffner et al. | |
| 6,111,163 A | 8/2000 | McCormack et al. | |
| 6,168,800 B1 | 1/2001 | Dobos et al. | |
| 6,245,401 B1 | 6/2001 | Ying et al. | |
| 6,255,359 B1 | 7/2001 | Agrawal et al. | |
| 6,261,674 B1 | 7/2001 | Branham et al. | |
| 6,265,059 B1 | 7/2001 | Kono et al. | |
| 6,268,048 B1 | 7/2001 | Topolkaraev et al. | |
| 6,329,454 B1 * | 12/2001 | Krabbenborg | 524/252 |
| 2004/0091752 A1 * | 5/2004 | Morman et al. | 428/910 |

* cited by examiner

FILM HAVING HIGH BREATHABILITY INDUCED BY LOW CROSS-DIRECTIONAL STRETCH

This application is a divisional of U.S. application Ser. No. 09/751,414, filed on Dec. 28, 2000 which claims benefit of 60/201,830 filed May 3, 2000.

FIELD OF THE INVENTION

This invention is directed to breathable films and laminates containing them. Most of the moisture vapor breathability is induced by stretching the films by a small amount in the cross direction.

BACKGROUND OF THE INVENTION

Laminates which are breathable to water vapor but substantially impermeable to liquid water are known in the art, and are commonly used in diaper backings, other personal care absorbent garments, medical and industrial protective garments, and the like. These laminates may be composed of a breathable, stretch-thinned filled film and a spunbond web. The breathable film can be formed by blending one or more polyolefins with an inorganic particulate filler, forming a film from the mixture, and stretching the film to cause void formation around the filler particles. The resulting film may have thin polymer membranes around the filler particles which permit molecular diffusion of water vapor, while the overall film substantially blocks transmission of liquid water, or may have micropores going through the film. The breathable film can be laminated to a nonwoven web, for instance, a spunbond web, by thermal or adhesive bonding. The spunbond web adds abrasion resistance, strength and integrity to the breathable laminate, and provides a soft, cloth-like feel.

One trend affecting the personal care absorbent garment industry, and the protective garment industry, involves the demand and need for products with higher breathability to water vapor, which retain or increase the barrier to water, blood and other liquid substances. This trend reflects the demand for increased wearer comfort without loss of barrier performance. Another trend affecting these industries involves the demand and need for products having better fit, which conform to the contours of the wearer's body.

Still another trend involves the demand and need for products which are less expensive to produce, and which use less materials without sacrificing desirable product characteristics. Still another trend involves the demand and need for laminates having higher breathability to moisture vapor in selected regions of the laminates. In diapers and other pant-like absorbent articles, liquid can accumulate in the crotch region. When this happens, heat from the wearer's body can cause the space between garment and the wearer to become saturated with water vapor, facilitating the occurrence of diaper rashes and other skin irritations. The best way to effectively vent the water vapor is through other regions of the garment which are not affected by the pool of liquid in the crotch.

SUMMARY OF THE INVENTION

The present invention is directed to a breathable film, and a breathable laminate including the film and at least one nonwoven web. The film has a first state in which it has not been extended in the cross-direction, and a second state in which it has been extended by 25% in the cross-direction. The film has a first water vapor transmission rate (WVTR) of at least 500 grams/m$^2$-24 hours in the first state, and a second WVTR in the second state, determined from the WVTR test procedure described below. The second WVTR in the second state is at least about 225% of the first WVTR, and is not less than about 4000 grams/m$^2$-24 hours. The large increase in WVTR between the first state and the second state occurs solely as a result of stretching the film by about 25% in the cross-direction.

The present invention is also directed to a breathable laminate which exhibits similar properties. The nonwoven web is selected, and is bonded to the breathable film, so as not to substantially impair the breathability of the film. In essence, the breathability of the laminate is determined by the breathability of the film, although the WVTR values may be somewhat lower for the laminate depending on the bonding technique employed. The laminate has a first state in which it has not been extended in the cross-direction, and a second state in which the laminate (including the film) has been extended by about 25% in the cross-direction of the film. The laminate has a first WVTR in the first state which is at least 500 grams/m$^2$-24 hours, determined from the WVTR test procedure described below. The laminate has a second WVTR in the second state which is at least 225% of the first WVTR, and is not less than about 4000 grams/m$^2$-24 hours.

The breathable laminate can be used in a wide variety of personal care absorbent articles and protective garments. In one embodiment, the laminate is used as a backsheet in a disposable diaper or other pant-like absorbent garment. The diaper or other pant-like garment is initially undersized, representing a material savings. To don the garment on a wearer, the front and back regions in the garment (including the laminate) are stretched by about 25% of the original width of the laminate, in the cross-direction of the film. This stretching causes the front and back regions to have substantially higher WVTR than the crotch region, which is not significantly stretched during donning.

With the foregoing in mind, it is a feature and advantage of the invention to provide a breathable film, and a corresponding film/nonwoven web laminate, to which high moisture vapor breathability can be induced by only minor stretching in the cross-direction of the film.

It is also a feature and advantage of the invention to provide a garment, such as a pant-like absorbent garment, to which selected regions of high breathability can be induced by minor stretching occurring during donning of the garment.

The foregoing and other features and advantages of the invention will become further apparent from the following detailed description of the presently preferred embodiments.

Definitions

The term "extendible" is used herein to mean a material which upon application of a stretching force, can be extended in a particular direction (e.g., the cross-direction), to a stretched dimension (e.g., width) which is at least 25% greater than an original, unstretched dimension. When the stretching force is removed after a one-minute holding period, the material preferably does not retract, or retracts by not more than 30% of the difference between the stretched dimension and the original dimension. Thus, a material having a width of one meter, which is extendible in the cross direction, can be stretched to a width of at least 1.25 meters. When the stretching force is released, after holding the extended width for one minute, a material stretched to a width of 1.25 meters will preferably not retract, or will retract to a width of not less than 1.175 meters. Extendible materials are different from elastic materials, the latter tending to retract most of the way to their original dimension when a stretching force is released. The stretching force can be any force sufficient to extend the material to between 125% of its original dimension, and its maximum stretched dimension in the selected direction (e.g., the cross direction) without rupturing it.

The "percent retraction" is determined when an extended material is relaxed to where the retractive force drops below 10 grams for a 3-inch wide sample. "Percent permanent set" is 100 minus "percent retraction."

The term "inelastic" refers both to materials that do not stretch by 25% or more and to materials that stretch by that amount but do not retract by more than 30%. Inelastic materials include extendible materials, as defined above, as well as materials that do not extend, e.g., which tear when subjected to a stretching force.

The term "machine direction" as applied to a nonwoven web, refers to the direction of travel of a conveyor passing beneath the spinnerette or similar extrusion or forming apparatus for the filaments, which causes the filaments to have primary orientation in the same direction. While the filaments may appear wavy, or even randomly oriented in a localized section of a nonwoven web, they usually have an overall machine direction of orientation which was parallel to the movement of the conveyor that carried them away from the extrusion or forming apparatus.

The term "machine direction" as applied to a film, refers to the direction on the film that was parallel to the direction of travel of the film as it left the extrusion or forming apparatus. If the film passed between nip rollers or chill rollers, for instance, the machine direction is the direction on the film that was parallel to the surface movement of the rollers when in contact with the film.

The term "machine direction" as applied to a laminate including at least one film and at least one nonwoven web, refers to the machine direction of the film component of the laminate.

The term "cross direction" for a nonwoven web, film, or laminate refers to the direction perpendicular to the machine direction. Dimensions measured in the cross direction are referred to as "width" dimensions, while dimensions measured in the machine direction are referred to as "length" dimensions.

The terms "breathable film," "breathable laminate" or "breathable outer cover material" refer to a film, laminate, or outer cover material having a water vapor transmission rate ("WVTR") of at least about 500 grams/m$^2$-24 hours, using the WVTR Test Procedure described herein. The term "higher breathability" simply means that a second material has a higher WVTR than a first material. Breathable materials typically rely on molecular diffusion of vapor, or vapor passage through micropores, and are substantially liquid impermeable.

The term "liquid water-permeable material" refers to a material present in one or more layers, such as a nonwoven fabric, which is porous, and which is liquid water permeable due to the flow of water and other aqueous liquids through the pores. The spaces between fibers or filaments in a nonwoven web can be large enough and frequent enough to permit leakage and flow of liquid water through the material.

The term "nonwoven fabric or web" means a web having a structure of individual fibers or threads which are interlaid, but not in a regular or identifiable manner as in a knitted fabric. Nonwoven fabrics or webs have been formed from many processes such as, for example, meltblowing processes, spunbonding processes, air laying processes, coforming processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91.)

The term "microfibers" means small diameter fibers typically having an average fiber denier of about 0.005–10. Fiber denier is defined as grams per 9000 meters of a fiber. For a fiber having circular cross-section, denier may be calculated as fiber diameter in microns squared, multiplied by the density in grams/cc, multiplied by 0.00707. For fibers made of the same polymer, a lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 calculated as ($15^2 \times 0.89 \times 0.00707 = 1.415$). Outside the United States the unit of measurement is more commonly the "tex," which is defined as the grams per kilometer of fiber. Tex may be calculated as denier/9.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 1.0 denier, and are generally self bonding when deposited onto a collecting surface.

The term "film" refers to a thermoplastic film made using a film extrusion process, such as a cast film or blown film extrusion process. This term includes films rendered microporous by mixing polymer with filler, forming a film from the mixture, and stretching the film.

The term "microporous" refers to films having voids separated by thin polymer membranes and films having micropores passing through the films. The voids or micropores can be formed when a mixture of polymer and filler is extruded into a film and the film is stretched, preferably uniaxially in the machine direction. Microporous films tend to have water vapor transmission due to molecular diffusion of water vapor through the membranes or micropores, but substantially block the passage of aqueous liquids.

The term "polymer" includes, but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

The term "garment" includes pant-like absorbent garments and medical and industrial protective garments. The term "pant-like absorbent garment" includes without limitation diapers, training pants, swim wear, absorbent underpants, baby wipes, adult incontinence products, and feminine hygiene products.

The term "medical protective garment" includes without limitation surgical garments, gowns, aprons, face masks, and drapes. The term "industrial protective garment" includes without limitation protective uniforms and workwear.

The term "neck" or "neck stretch" interchangeably means that the fabric, nonwoven web or laminate is drawn such that it is extended under conditions reducing its width or its transverse dimension by stretching lengthwise or increasing the length of the fabric. The controlled drawing may take place under cool temperatures, room temperature or greater temperatures and is limited to an increase in overall dimension in the direction being drawn up to the elongation required to break the fabric, nonwoven web or laminate, which in most cases is about 1.2 to 1.6 times. When relaxed, the fabric, nonwoven web or laminate does not return totally to its original dimensions. The necking process typically involves unwinding a sheet from a supply roll and passing it through a brake nip roll assembly driven at a given linear speed. A take-up roll or nip, operating at a linear speed higher than the brake nip roll, draws the fabric and generates the tension needed to elongate and neck the fabric. U.S. Pat. No. 4,965,122 issued to Morman, and commonly assigned to the assignee of the present invention, discloses a reversibly necked nonwoven material which may be formed by necking the material, then heating the necked material, followed by cooling and is incorporated herein by reference in its entirety. The heating of the necked material causes additional crystallization of the polymer giving it a partial heat set. If the necked material is a spunbond web, some of the fibers in the web may become crimped during the necking process, as explained in U.S. Pat. No. 4,965,122.

The term "neckable material" or "neckable layer" means any material or layer which can be necked such as a nonwoven, woven, or knitted material, or a laminate containing one of them. As used herein, the term "necked material" refers to any material which has been drawn in at least one dimension, (e.g. lengthwise), reducing the transverse dimension, (e.g. width), such that when the drawing force is removed, the material can be pulled back to its original width. The necked material generally has a higher basis weight per unit area than the un-necked material. When the necked material is pulled back to its original width, it should have about the same basis weight as the un-necked material. This differs from stretching/orienting the film layer, during which the film is thinned and the basis weight is reduced. Preferred nonwoven webs for use in the invention are made from an inelastic polymer.

The term "percent neckdown" refers to the ratio determined by measuring the difference between the un-necked dimension and the necked dimension of the neckable material and then dividing that difference by the un-necked dimension of the neckable material.

DETAILED DESCRIPTION OF THE PRESENTLY PREFERRED EMBODIMENTS

Figure 1A:
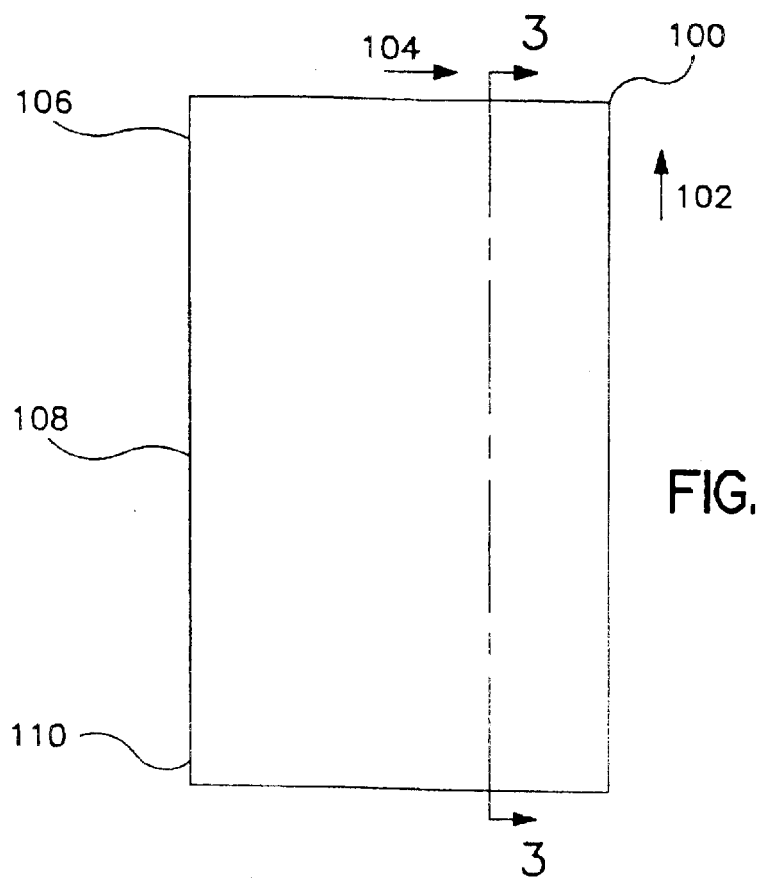
FIG. 1(a) is a top plan view of a microporous film of the invention which has not yet been stretched in the cross-direction.
Figure 1B:
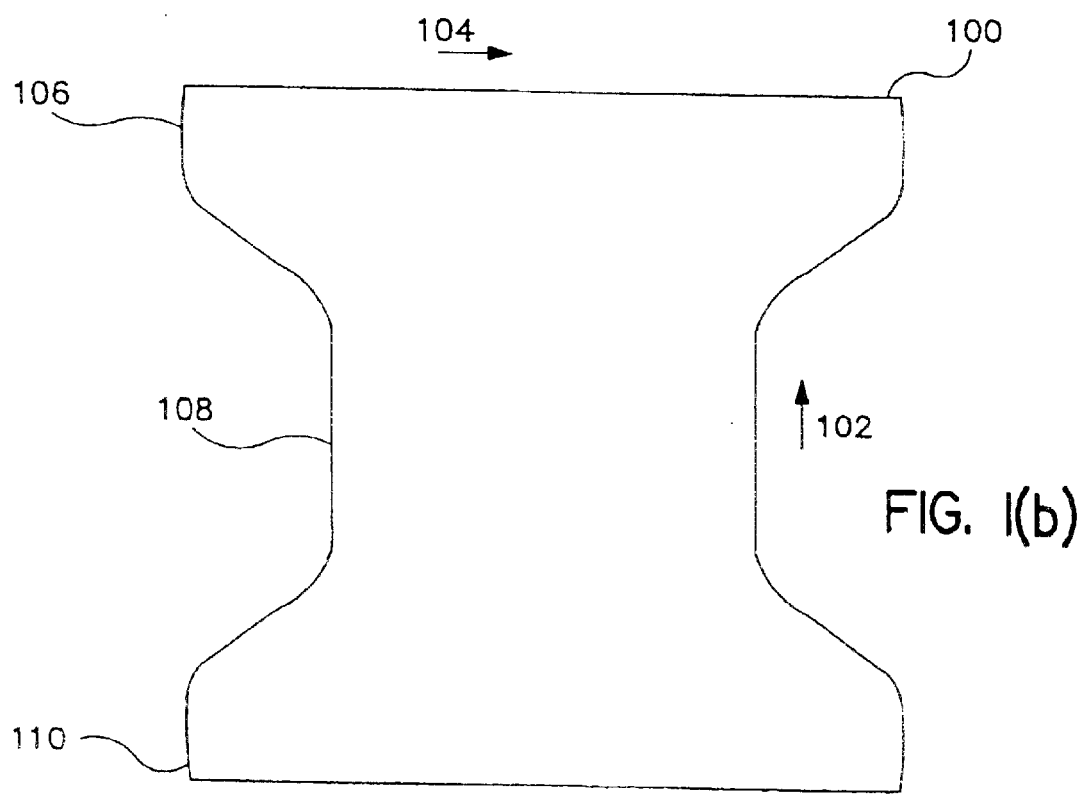
FIG. 1(b) illustrates the film of FIG. 1(a), stretched in the cross-direction at both end regions, but not in the middle, to impact high breathability at both end regions.
Figure 2:
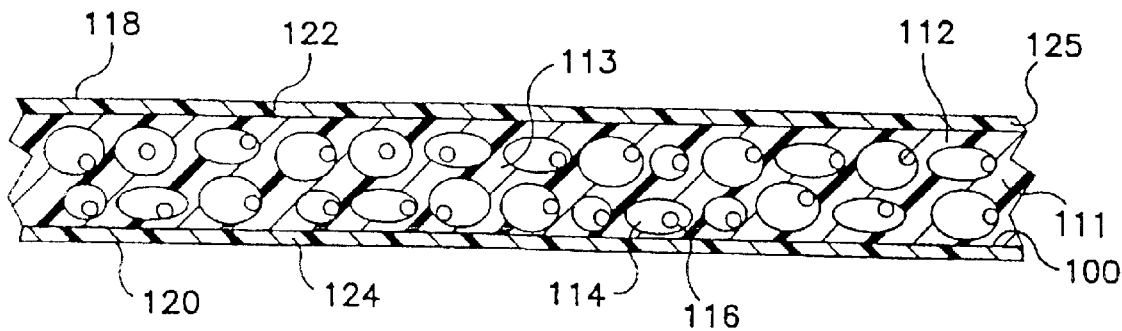
FIG. 2 is a sectional view of a microporous film, taken along line 3—3 in FIG. 1.

FIGS. 1(a), 1(b) and 2 illustrate a film 100 of the invention. Referring to FIG. 1(a), film 100 has a machine direction 102 and a cross-direction 104, and has a first end region 106, a central region 108, and a second end region 110. Film 100 as shown in FIG. 1(a) has not yet been stretched in the cross-direction 104. In this first state, film 100 may have a first WVTR of at least about 500 grams m$^2$-24 hours, suitably at least about 1000 grams/m$^2$-24 hours, desirably at least about 1500 grams/m$^2$-24 hours.

FIG. 1(b) illustrates the film 100 after both end regions 106 and 110 have been stretched in the cross-direction 104, suitably to about 125% of their original width. The configuration of film 100 shown in FIG. 1(b) corresponds to the type of stretching that would occur when film 100 is used in a backsheet of a diaper or other pant-like absorbent garment. The first and second end regions 106 and/or 110, which correspond to the front and/or back of the garment, would experience about a 25% cross-directional stretch (to about 125% of their initial width) during donning of the garment on a wearer. The central region 108, which corresponds to the crotch region of the garment, would not stretch in the cross-direction during donning. In accordance with the invention, the first and/or second end regions 106 and 110 (in the second state, after 25% cross-directional stretching) may have a second WVTR which is at least 225% of the first WVTR, suitably at least 250% of the first WVTR, desirably at least 300% of the first WVTR, with the second WVTR not being less than about 4000 grams/m$^2$-24 hours. Suitably, the second WVTR may be at least about 5500 grams/m$^2$-24 hours, desirably at least about 7000 grams/m$^2$-24 hours. The central region 106, which remains in the first state (unstretched in the cross-direction) retains the lower WVTR values indicated for the film of FIG. 1(a). In essence, the 25% cross-directional stretch causes a large increase in WVTR, in the selected regions.

The film of the invention is thus characterized both in terms of an order of magnitude increase in WVTR resulting from a 25% cross-directional stretch, and a relatively high WVTR following the 25% cross-directional stretch. If the film 100 (or portion thereof) has a relatively high first WVTR of, say, 2000 grams/m$^2$-24 hours before the cross-directional stretch, then the second WVTR of the stretched film (or stretched portion) is at least 225% of the first WVTR. However, if the film 100 has a relatively low first WVTR of, say, 500–1000 grams/m²-24 hours, then the second, post-stretching WVTR is at least 4000 grams/m²-24 hours and a higher order-of-magnitude increase is required.

After the cross-directional stretching, the highly breathable end regions of film 100 (as well as the central region) should remain substantially impermeable to liquid water. In order to achieve the high breathability resulting from low cross-directional stretching, while retaining liquid barrier, the film composition must be properly selected. The microporous film 100, which may be a single-layer film or a multilayer film, has a primary breathable layer. In a first embodiment, the primary breathable layer may be formed from a composition including a single-site catalyzed olefin polymer, a Ziegler-Natta catalyzed olefin polymer, and a particulate filler. Surprisingly, this composition has been found to yield a greater order of magnitude increase in film WVTR resulting from 25% cross-directional stretch than both a) an otherwise similar composition including the single-site catalyzed polymer and filler, without the Ziegler-Natta catalyzed polymer, and b) an otherwise similar composition including the Ziegler-Natta catalyzed polymer and filler, without the single-site catalyzed polymer. The film-forming composition should include about 10–55% by volume particulate filler and about 45–90% by volume total polymer, suitably about 15–45% by volume particulate filler and about 55–85% by volume total polymer, desirably about 25–40% by volume particulate filler and about 60–75% by volume total polymer. The term "volume" refers to the total volume occupied by the polymers and filler, and excludes air space. The large quantity of particulate filler, which is preferably homogeneously disposed among the polymer, aids in the formation of voids when the film is stretched. The voids are separated by thin polymer membranes which facilitate the transmission (i.e. diffusion) of water vapor while blocking the flow of liquid water.

The term "total polymer" includes both the single-site catalyzed olefin polymer and the Ziegler-Natta catalyzed olefin polymer, as well as other optimal polymer ingredients which do not prevent the film from having a first WVTR of at least 500 grams/m²-24 hours before cross-directional stretching, and a second WVTR after 25% cross-directional stretching which is a) at least 225% of the first WVTR, and b) not less than 4000 grams/m²-24 hours. The total polymer may include about 10–90% by weight at the single-site catalyzed olefin polymer and about 10–90% by weight of the Ziegler-Natta catalyzed olefin polymer, suitably about 25–75% by weight of the single-site catalyzed olefin polymer and about 25–75% by weight of the Ziegler-Natta catalyzed olefin polymer, desirably about 30–60% by weight of the single-site catalyzed olefin polymer and about 40–70% by weight of the Ziegler-Natta catalyzed olefin polymer.

Suitable olefin polymers include polyolefins, such as polyethylene, polypropylene, polybutene and the like, as well as olefin copolymers. Suitable olefin copolymers include copolymers having a major weight fraction (e.g. 70–99% by weight) ethylene and a minor weight fraction (e.g. 1–30% by weight) of a $C_3$–$C_{12}$ alpha-olefin comonomer. Such copolymers are commonly known as linear low density polyethylenes (where the density is about 0.900–0.935 grams/cm³) or very low density polyethylenes (where the density is about 0.870 to less than 0.900 grams/cm³). Suitable olefin copolymers also include copolymers having a major weight fraction (e.g. 70–99% by weight) propylene and a minor weight fraction (e.g. 1–30% by weight) of a $C_2$ or $C_4$–$C_{12}$ alpha-olefin comonomer. The olefin polymer should be selected so that the film is extendible in the cross-direction, meaning that it can be stretched by at least 25% of its initial width without rupture or tear, and will not retract by more than 30% of the difference between the stretched width and the initial width if the stretching force is removed.

Other examples of extendible olefin polymers include certain flexible polyolefins, for example propylene-based polymers having both atactic and isotactic propylene groups in the main polypropylene chain. Flexible polyolefins (FPO's) are sold by the Rexene Corporation. Also included are heterophasic propylene-ethylene copolymers sold as "catalloys" by the Himont Corporation. Heterophasic polymers are reactor blends formed by adding different levels of propylene and ethylene at different stages in the reactor. Heterophasic polymers typically include about 10–90% by weight of a first polymer segment A, about 10–90% by weight of a second polymer segment B, and 0–20% by weight of a third polymer segment C. Polymer segment A is at least about 80% crystalline and includes about 90–100% by weight propylene, as a homopolymer or random copolymer with up to 10% by weight ethylene. Polymer segment B is less than about 50% crystalline, and includes about 30–70% by weight propylene randomly copolymerized with about 30–70% by weight ethylene. Optional polymer segment C contains about 80–100% by weight ethylene and 0–20% of randomly copolymerized propylene.

Olefin polymers made using single-site catalysts have a very narrow molecular weight range. Polydispersity numbers (Mw/Mn) of below 4 and even below 2 are possible for metallocene-produced polymers. These polymers also have a controlled short chain branching distribution compared to otherwise similar Ziegler-Natta produced type polymers. It is also possible using a metallocene catalyst system to control the isotacticity of the polymer quite closely. In general, polyethylene polymers and copolymers having a density of 0.900 grams/cc or greater tend to be less extendible, while those having a density below 0.900 grams/cc are more extendible. In general, polypropylene polymers and copolymers containing 0–10% of an ethylene or other alpha-olefin comonomer tend to be less extendible, while propylene-alpha olefin copolymers containing more than 10% comonomer are more extendible.

Commercial production of single-site catalyzed polymers is somewhat limited but growing. Such polymers are available from Exxon-Mobil Chemical Company of Baytown, Tex. under the trade name ACHIEVE for polypropylene based polymers and EXACT and EXCEED for polyethylene based polymers. Dow Chemical Company of Midland, Mich. has polymers commercially available under the name AFFINITY. These materials are believed to be produced using non-stereo selective metallocene catalysts. Exxon-Mobil generally refers to their catalyst technology as single site or metallocene catalysts while Dow refers to theirs as "constrained geometry" catalysts under the name INSITE to distinguish them from traditional Ziegler-Natta catalysts which have multiple reaction sites. Other manufacturers such as Fina Oil, BASF, Amoco, Hoechst and Mobil are active in this area and it is believed that the availability of polymers produced according to this technology will grow substantially in the next decade.

Without wishing to be bound by theory, it is believed that films produced from single-site catalyzed olefin polymers and filler and stretched only in the machine direction to about 1.1–7.0 times their initial length, have relatively lower breathability due to the fact that the single-site catalyzed polymers are both tenacious and extendible, and do not readily form voids. Films produced from Ziegler-Natta catalyzed olefin polymers and filler, and similarly stretched in the machine direction, form voids more readily and exhibit higher breathability. The films of the invention, which contain both polymer types in addition to the filler, somehow combine these properties by exhibiting relatively lower WVTR when stretched only in the machine direction, yet much higher WVTR when further stretched only slightly in the cross-direction.

FIG. 2 illustrates a cross-section of a breathable extendible microporous film 100 that can be laminated to a nonwoven web to form a breathable laminate, as described below. The breathable microporous film 100 can include a primary microporous core layer 112 formed from the composition described above. The breathable layer 112 may be combined with two thinner skin layers 122 and 124 which are used for bonding. Alternatively, the film 100 may include a primary microporous core layer 112, and only one skin layer 122 or 124, or no skin layers.

The microporous layer 112 includes a polymer matrix 111, a plurality of voids 114 within the matrix surrounded by relatively thin microporous membranes 113 defining tortuous paths, and one or more filler particles 116 in each void 114. The layer 112 is microporous and breathable, wherein the microporous membranes 113 between the voids readily permit molecular diffusion of water vapor from a first surface 118 to a second surface 120 of the film 100. Alternatively, some or all of the micropores can pass through the film, or can be interconnected to provide through-passages. The polymer matrix 111 may include both the single-site catalyzed olefin polymer and the Ziegler-Natta catalyzed olefin polymer, as discussed above.

The filler particles 116 can include any suitable inorganic or organic filler. The filler particles 116 are preferably small to produce micropores, in order to maintain liquid water barrier of the film 100. Generally, the filler particles should have a mean particle diameter of about 0.1–7.0 microns, preferably about 0.5–5.0 microns, most preferably about 0.8–2.0 microns. Suitable fillers include without limitation calcium carbonate, non-swellable clays, silica, alumina, barium sulfate, sodium carbonate, talc, magnesium sulfate, titanium dioxide, zeolites, aluminum sulfate, diatomaceous earth, magnesium sulfate, magnesium carbonate, barium carbonate, kaolin, mica, carbon, calcium oxide, magnesium oxide, aluminum hydroxide and polymer particles. Calcium carbonate is a presently preferred filler.

The filler particles 116 may be coated with a minor quantity (e.g. up to 2% by weight) of a fatty acid or other material to ease their dispersion in the polymer matrix. Suitable fatty acids include without limitation stearic acid, or a larger chain fatty acid such as behenic acid.

The polymer composition, filler content, filler particle size and degree of stretching are factors which help determine the breathability and liquid barrier of the extendible microporous film 100 in the laminate. Generally, the oriented microporous film 100 will be less than about 50 microns thick, preferably less than about 30 microns thick, most preferably less than about 20 microns thick. The film 100 may be uniaxially stretched in the machine direction to about 1.1–7.0 times its original length to cause breathability, preferably to about 1.5–6.0 times its original length, most preferably to about 2.5–5.0 times its original length prior to lamination to a nonwoven web. This machine direction stretching, which is reflected in the first film state shown in FIG. 1(a), causes the film to have a low level of breathability, i.e., an WVTR of not more than about 1000 g/m²-24 hours. Stretching temperatures may range from about 38–150° C. depending on the specific polymers employed, and are preferably about 70–95° C. The film 100 can be prepared by cast or blown film coextrusion of the layers, by extrusion coating, or by any conventional layering process.

In the embodiment of FIG. 2, the microporous breathable film layer 112 is adjacent one or two relatively thin outer skin layers 122 and 124, in a two or three-layer extendible film 100. The inclusion of one or two skin layers improves film processability and can also contribute heat seal properties to the breathable extendible film 100. The polymers in the outer layers 122 and 124 can be the same or different than the polymers in the microporous layer 112. Preferably, the polymers in the outer layer or layers are extendible, have a lower softening point than in the microporous layer 112, and contribute to the heat sealability of the film 100. To facilitate breathability, the skin layers 122 and 124 may contain a particulate filler in any quantity up to the same amount as the microporous core layer 112, and the skin layers may be microporous as well after the film is machine direction orientated.

Also, the thickness and composition of the outer layers 122 and 124 should be selected so as not to substantially impair the moisture transmission through the breathable film 100. This way, the microporous core layer 112 may determine the breathability of the entire film. To this end, the skin layer 122 and 124 is generally less than about 10 microns thick, preferably less than about 5 microns thick. The combined skin layers should constitute no more than 25% of the entire film thickness, and preferably constitute about 2–15% of the film thickness, more preferably 3–5% of the total film thickness. Suitable extendible skin layer polymers having low softening points include amorphous metallocene or Ziegler Natta-catalyzed copolymers of ethylene with a $C_3$–$C_{20}$ alpha-olefin comonomer, having a density less than about 0.89 grams/cc. Also suitable are amorphous poly alpha-olefin (APAO) polymers which can be random copolymers or terpolymers of ethylene, propylene, and butene, and other substantially amorphous or semi-crystalline propylene-ethylene polymers. Also included are ethylene vinyl acetates, propylene vinyl acetates, ethylene methyl acrylates, and blends of any of the foregoing polymers.

As explained above, one embodiment of the invention involves combining a first polymer A which is a single-site catalyzed olefin polymer, with a second polymer B which is a Ziegler-Natta catalyzed olefin polymer, and a filler, and using this composition to form the primary breathable microporous layer 112 of the film 100, or the only layer if film 100 is monolayer. In a second embodiment, the first polymer A may be a higher density olefin polymer and the second polymer B may be a lower density olefin polymer. The two polymers may be combined with a particulate inorganic filler and with each other in the same compositional ranges described above. In particular, the first polymer A may be a very low density polyethylene having a density of 0.870 to less than 0.900 grams/cm³, and the second polymer B may be a linear low density polyethylene having a density of 0.900–0.935 grams/cm³.

The second embodiment of the film-forming composition may operate by a similar principle as the first embodiment of the film-forming composition. The lower density olefin polymer is more readily extendible and does not separate easily from the filler particles to form voids, when the film is stretched. The higher density olefin polymer is stiffer and readily forms voids, yielding higher breathability, even when the film is only stretched in the machine direction. By combining the two polymers and filler, a film is obtained which exhibits low WVTR when stretched only in the machine direction, and much higher WVTR when subsequently stretched by only 25% in the cross-direction.

In a third embodiment, the principles of the first and second embodiments may be combined. The first polymer A may be a single-site catalyzed olefin polymer which also has a lower density, and the second polymer B may be a Ziegler-Natta catalyzed olefin polymer which also has a higher density. For instance, the first polymer A may be a single-site catalyzed very low density polyethylene having a density of 0.870 to less than 0.900 grams/cm$^3$. The second polymer B may be a Ziegler-Natta catalyzed linear low density polyethylene having a density of 0.900 to 0.935 grams/cm$^3$. The two polymers may be combined with each other and a particulate filler using the same compositional ranges described above for the first embodiment.

In a typical case, the film 100 will be oriented only in the machine direction before being laminated to a nonwoven web, and will be stretched slightly in the cross-direction after lamination to yield a greatly improved WVTR. This means that the nonwoven web must also be capable of extending in the cross-direction, to accommodate the stretching of the film. Typically, the film and nonwoven web will be bonded together with the machine direction of the film substantially aligned with the machine direction of the nonwoven web. The bonding may be accomplished using any technique which minimizes disruption of the moisture vapor transmission through the film. Suitable techniques include thermal point bonding, ultrasonic point bonding, adhesive pattern bonding, adhesive spray bonding, and other techniques where the bonded areas cover preferably less than about 25% of the interface between the film and nonwoven web.

Figure 3:
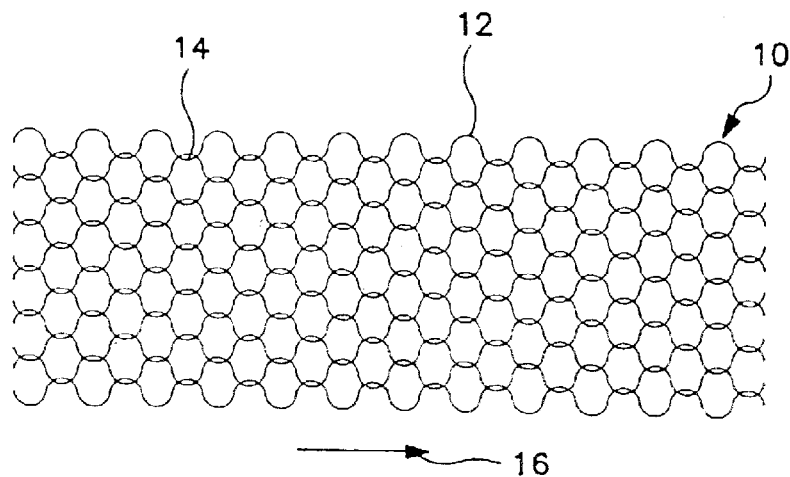
FIG. 3 illustrates a top view of a fibrous nonwoven web, which can be a spunbond web, which has not been necked.

A variety of nonwoven webs are suitable for use in the laminate of the invention. Referring to FIG. 3, a nonwoven web 10, which can be a spunbond web, includes a plurality of individual thermoplastic fiber elements 12 intermittently bonded together using a bonding pattern which, in this instance, includes a plurality of point bonds 14. The individual fibers 12 appear to have a wavy or somewhat random orientation when viewed on a microscopic scale. When viewed on a macroscopic scale, so that the entire lengths of fibers 12 are visible, the fibers 12 have an overall primary direction of orientation which is parallel to a machine direction, represented by arrow 16. If the nonwoven web is spunbond, it may be intentionally produced with high machine-direction filament orientation and thermal bonds oriented predominantly in the machine direction. This will provide the spunbond web with inherent cross-directional extendibility, much like that existing in a conventional bonded carded web.

Figure 4:
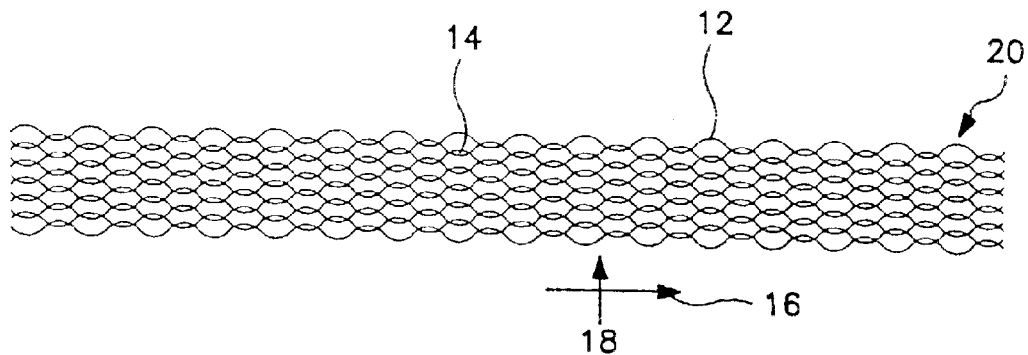
FIG. 4 illustrates a top view of a fibrous nonwoven web, which can be a spunbond web, which has been necked.

The nonwoven web is preferably a spunbond web, but can also be a meltblown web, a bonded carded web, an air laid web, or a laminate or composite including one or more nonwoven webs. The nonwoven web may also be formed or modified using a hydraulic entangling process. In one embodiment, the nonwoven web or composite including it, is neckable, as defined above. FIG. 4 illustrates a top view of a necked nonwoven material 20, which can be the nonwoven web 10 stretched in the machine direction 16 prior to lamination to the film 100, to cause elongation of the web in the machine direction 16 and narrowing, or neck-in, in the cross direction 18. As shown in FIG. 4, necking causes the individual filaments 12 to become more aligned with each other, and closer to each other. When a neckable nonwoven web or composite is employed, it should have a percent neck-down of at least about 15%, more preferably about 25–75%, most preferably about 35–65%. Prior to necking, the nonwoven web 10 should have a basis weight of about 0.05–4.0 ounces per square yard. ("osy"), preferably about 0.3–2.0 osy, more preferably about 0.4–1.0 osy.

When a neckable nonwoven web is used, the nonwoven web can be constructed from either a variety of polymers. Examples of suitable non-extendible and less extendible polymers include, without limitation, certain polyolefins, polyamides, and polyesters. Preferred polymers (whether extendible or not) include polyolefins, such as polypropylene and/or polyethylene. Other suitable polymers include linear low density polyethylene copolymers, and copolymers of propylene with up to about 10% by weight of a $C_2$ or $C_4$–$C_{12}$ alpha-olefin comonomer.

In another embodiment, the nonwoven web 10 is made of an extendible polymer composition, and need not be necked prior to lamination with the film 100. Suitable polymers include, without limitation, any of the extendible polymers and blends listed above for the film-forming composition. The extendible fibers 12 may be composed of a blend or other combination of an extendible and non-extendible polymer, so long as the extendible polymer is present in sufficient quantity to render the nonwoven web extendible in the cross-direction.

In a third embodiment, the cross direction extendible nonwoven web 10 is made of fibers 12 that are crimped. A wide variety of crimping processes are known in the art. Crimped fibers have accordion-like or spring-like undulations or microundulations so that when the fibers are extended, they straighten out and/or the undulations are reduced in amplitude. When crimped fibers are used, the polymer of construction need not be extendible, i.e., may be extendible or not extendible.

In yet another embodiment, the nonwoven is formed so that the fibers have very high machine direction (MD) and very little cross direction (CD) orientation. The fibers are then bonded so as to minimize CD bonding of the fibers. This allows the material to extended in the CD. An example of such a material is a bonded carded web (BCW) nonwoven that has high CD extendibility and low MD extendibility. Other nonwovens, such as spunbonds, can be made to perform like BCW's by forming the spunbond fibers so that the fibers are highly oriented in the MD and bond the filaments with a bond pattern so that the material can readily extend in the CD. Such a bond pattern would have lower percent bond area (less than 25%) with the bonds lined up predominately in the MD. Thus there are columns of fibers in the MD which are not bonded adjacent to columns of fibers in the MD that are. The unbonded fibers allow the nonwoven to readily extend in the CD while the bonded fibers give the material strength and abrasion resistance. BCW materials are described further in *Encyclopedia of Polymer Science and Engineering*, Vol. 10, Pages 211–212, Wiley & Sons (1987), which is incorporated by reference.

Any nonwoven web is suitable so long as it accommodates the cross-directional stretching of the film in the laminate. A necked nonwoven web accomplishes this by returning toward its original, pre-necked state during cross-directional stretching of the laminate. A web made of extendible polymer simply stretches in the cross-direction with the film. A web of crimped fibers extends in the cross-direction by straightening out the fibers. A web with high machine direction orientation can extend in the cross-direction by increasing the spacing between unbonded portions of adjacent fibers.

The nonwoven web should be selected so as not to substantially impair or lower the WVTR contributed by the film. The bonding technique between the film and web should also be selected so that not more than about 15–25% of the interface between the film and web is covered with adhesive or thermally bonded regions, so as not to substantially impair the WVTR. Before the 25% cross-directional stretch, the laminate may have a first WVTR of at least about 500 grams/m²-24 hours, suitably at least about 1000 grams/m²-24 hours, desirably at least about 1500 grams/m²-24 hours. After the 25% cross-directional stretch, the laminate may have a second WVTR which is at least 225% of the first WVTR, suitably at least 250% of the first WVTR, desirably at least 300% of the first WVTR, with the second WVTR not being less than about 4000 grams/m²-24 hours. Suitably, the second WVTR maybe at least about 5500 grams/m²-24 hours, desirably at least about 7000 grams/m²-24 hours.

Figure 5:
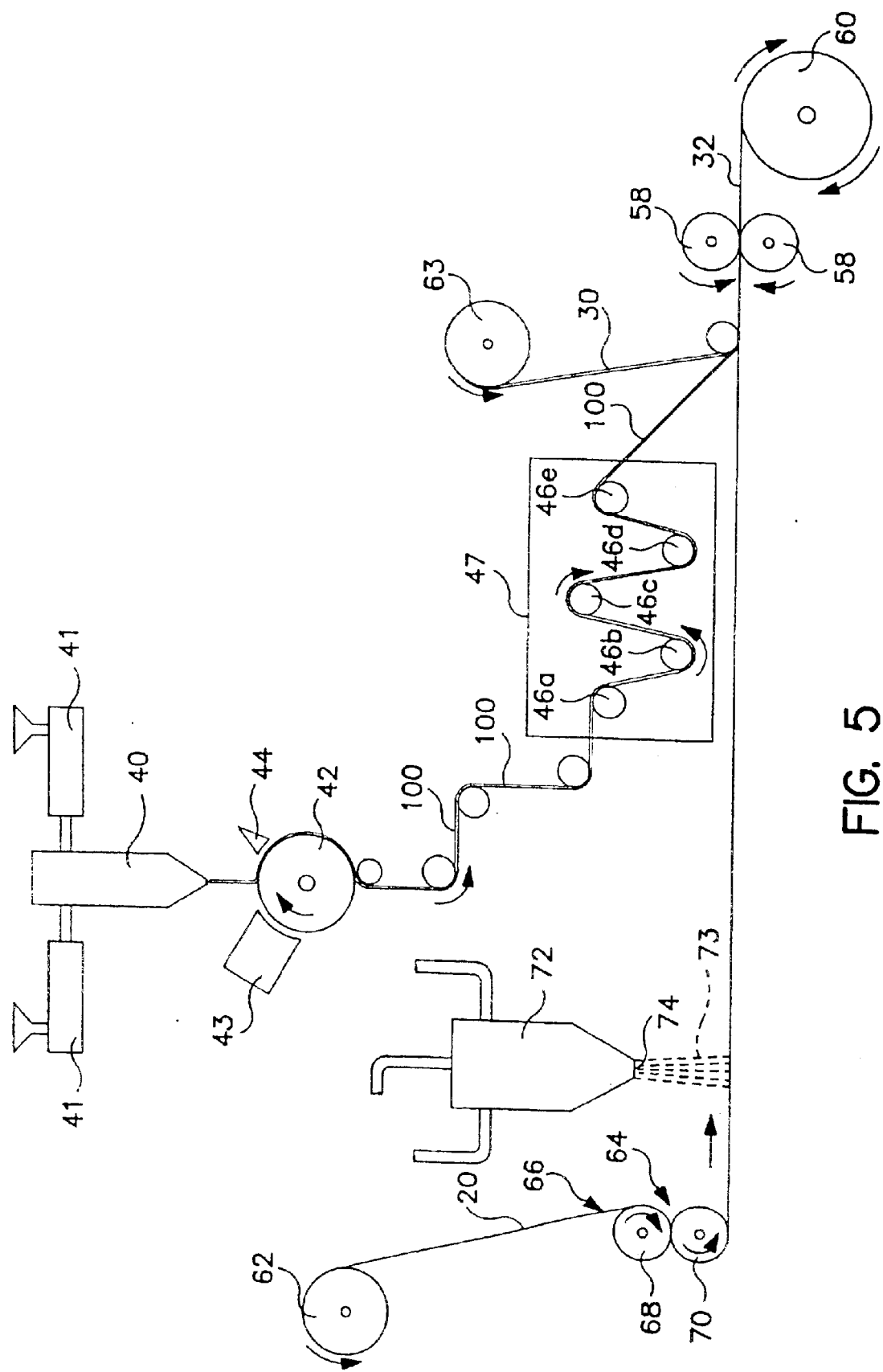
FIG. 5 schematically illustrates a process that can be used to form the breathable laminates of the invention.

FIG. 5 illustrates an integrated process for forming a multilayer breathable film and a laminate. Referring to FIG. 5, film 100 is formed from a film coextrusion apparatus 40 such as a cast or blown unit which could be in-line or off-line. Typically the apparatus 40 will include two or three extruders 41. To make the core layer, filled resin including the polymer matrix material and filler is prepared in a mixer (not shown) and directed to an extruder 41. To make each skin layer, similar additional mixing apparatus (not shown) and extrusion apparatus 41 can be used to mix the incompatible polymer components and extrude them as skin layers on one or both sides of the core layers. The multilayer film 100 is extruded onto a chill roller 42, which cools the film 100. A vacuum box 43 adjacent the chill roller creates a vacuum on the surface of the chill roller to help maintain the film close to the surface of the chill roller. Air knives or electrostatic pinners 44 also urge the film 100 against the roller surface.

From the film extrusion apparatus 40 or off-line rolls supplied, the multilayer film 100 is directed to a film stretching unit 47 which can be a machine direction oriented, commercially available from vendors including the Marshall and Williams Co. of Providence, R.I. Apparatus 47 has a plurality of stretching rollers 46a–e, which progressively stretch and thin the film in the machine direction, which is the direction of travel of the film. The rollers 46a–e, which are heated to the desired stretching temperature, apply an amount of stress and progressively stretch the multilayer film 100 to a stretched length where the core layer 112 becomes microporous and breathable, and the skin layers 122 and 124 become sufficiently thin, and perhaps microporous, so as not to inhibit overall film breathability. While the apparatus 47 is shown with five stretching rollers 46a–e, the number of rollers may be greater or less depending on the level of stretch desired and the amount of stretching between each pair of rollers.

Advantageously, the film 100 may be uniaxially stretched prior to lamination to about 1.1–7.0 times its original length, particularly about 1.5–6 times its original length, suitably about 2.5–5 times its original length, using an elevated stretch temperature as explained above. The elevated stretch temperature can be sustained by heating some or all of the stretch rollers 46a–e. The optimum stretch temperature varies with the core layer and skin layer polymers of film 100, and is generally below the melting temperature of the matrix polymer in the core layer 112.

The film 100 may be laminated to the nonwoven web, or webs, using conventional adhesive bonding or thermal bonding techniques known in the art. Referring again to FIG. 5, film 100 may be laminated to nonwoven web 20 immediately after the film is stretched. In one embodiment, a neckable nonwoven web 20, which can be a spunbond web, is unwound from a supply roll 62. The neckable material 20 then passes through the nip 64 of S-roll arrangement 66, formed by a stack of rollers 68–70, in a reverse S-wrap path as shown by the arrows. Rollers 68 and 70 turn at a faster circumferential speed than upstream supply roller 62, causing tensioning and neck-in of web 20. The tensioned, necked material can be passed under spray equipment 72 (e.g., a meltblown die) which sprays adhesive 73 through die head 74 onto a surface of web 20. With or without the adhesive treatment, the necked web 20 can then be joined to multilayer film 100 and bonded between calender rollers 58, which can be heated if necessary. The rollers 58 can be smooth, patterned, or one of each. The rollers 58 can be of steel, rubber, or another suitable material. The film 100 in FIG. 5 is simultaneously bonded on its other side to a second material 30 originating from supply roll 63. The second extendible material 30 may be a second nonwoven web, or another film layer. The resulting laminate 32 is wound and stored on a supply roll 60. In addition to the described bonding technique, other bonding techniques (e.g., other thermal, adhesive or ultrasonic bonding) may be employed.

After the film and nonwoven web are combined, the resulting laminate can be easily stretched in the cross-direction to cause greatly improved breathability. Alternatively, the laminate may be selectively stretched in the cross-direction in certain regions of the laminate, to cause improved breathability only in those regions. Often, the easy cross-directional stretch will occur after the laminates have been converted into garments, and the garments are put into use. The cross-directional stretching, which can typically be accomplished at room temperature by hand, may be on the order of 25% or more (resulting in an increase in the width of the laminate, or selected regions of the laminate, of 25% or more). This permits the manufactured garments to be somewhat undersized, resulting in a material savings. The effective size of the garments can then be increased during donning, when the garment is stretched or selectively stretched to conform to the contours of a wearer.

The cross-direction extendible, breathable laminate may be used in a variety of pant-like absorbent garments, including without limitation diapers, training pants, swimwear, absorbent underpants, adult incontinence products, feminine hygiene products, and the like. When these garments are installed, the cross-directional stretching of the breathable laminate (which may be used as a backsheet) occurs primarily in and below the front and/or back waist regions, causing these regions to have significantly enhanced WVTR. The crotch region is not stretched, or is stretched a lesser extent, and remains less breathable. The cross-direction extendible, breathable laminate can also be used in protective garments, including medical garments and industrial protective garments. Medical garments include surgical garments, gowns, aprons, face masks, absorbent drapes, and the like. Industrial protective garments include protective uniforms, workwear, and the like.

Test Procedures

1. WVTR

Test Procedure

A suitable technique for determining the WVTR (water vapor transmission rate) value of a film or laminate material of the invention is the test procedure standardized by INDA (Association of the Nonwoven Fabrics Industry), number IST-70.4-99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR" which is incorporated by reference herein. The INDA procedure provides for the determination of WVTR, the permeance of the film to water vapor and, for homogeneous materials, water vapor permeability coefficient.

The INDA test method is well known and will not be set forth in detail herein. However, the test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W Model 100K manufactured by Mocon/Modern Controls, Inc., Minneapolis, Minn. A first test is made of the WVTR of the guard film and the air gap between an evaporator assembly that generates 100% relative humidity. Water vapor diffuses through the air gap and the guard film and then mixes with a dry gas flow which is proportional to water vapor concentration. The electrical signal is routed to a computer for processing. The computer calculates the transmission rate of the air gap and the guard film and stores the value for further use.

The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also, again, this mixture is carried to the vapor sensor. The computer than calculates the transmission rate of the combination of the air gap, the guard film, and the test material. This information is then used to calculate the transmission rate at which moisture is transmitted through the test material according to the equation:

$$TR^{-1}_{test\ material} = TR^{-1}_{test\ material,\ guardfilm,\ airgap} - TR^{-1}_{guardfilm,\ airgap}$$

Calculations:
WVTR: The calculation of the WVTR uses the formula:

$$WVTR = F p_{sat}(T) RH / A p_{sat}(T)(1-RH))$$

where:
F=The flow of water vapor in cc/min.,
$p_{sat}(T)$=The density of water in saturated air at temperature T,
RH=The relative humidity at specified locations in the cell,
A=The cross sectional area of the cell, and,
$p_{sat}(T)$=The saturation vapor pressure of water vapor at temperature T.

2. Hydrohead Resistance

The hydrohead resistance is a measure of liquid pressure resistance, which is the ability of a film or laminate to withstand application of a load of liquid without fracturing, bursting or tearing. The liquid pressure resistance of a film depends on its thickness, material composition, how it is made and processed, the surrounding environment and method of testing. Hydrohead values reported herein are measured according to the Hydrostatic Pressure Test described in Method 5514 of Federal Test Methods Standard No. 191A, which is equivalent to AATCC Test Method 127–89 and INDA Test Method 80.4–92, and which is incorporated herein by reference.

Some of the test results below are for "supported" test specimens. For these specimens, the test material was supported by a nylon net (T-246) purchased from Walmart. The netting was approximately 0.1 mm thick and was made up of nylon threads in hexagonal shapes in the form of a honeycomb. Each hexagonal shape was approximately 4 mm across.

EXAMPLES

Examples 1–3

Samples of three different films were prepared on a cast extrusion line and stretch oriented in the machine direction to about 4.0 times their original length. Prior to stretching, each film had a thickness of 1.8–1.9 mils. The stretching temperature was about 190° C. for each film. The stretched films were annealed at 210° C. The films had the following compositions.

Example 1

Control

The film of Example 1 was a three-layer A-B-A cast film sold as Huntsman Type 1885, available from Huntsman Packaging Corp., 199 Edison Drive, Washington, Ga. 30763. The film had a core layer containing 42% by weight (69% by volume) Ziegler-Natta catalyzed linear low density polyethylene. The polyethylene had an octene comonomer, and a density of 0.918 grams/cm$^3$. The core layer also contained 58% by weight (31% by volume) of stearic acid-coated calcium carbonate particles having a mean diameter of about 1 micron and a top cut of 7 microns. The film had two skin layers, each containing a mixture of 50.4% by weight ethylene vinyl acetate (28% by weight vinyl acetate content), 45.1% by weight of a heterophasic combination of propylene-ethylene copolymers commercially known as Montell KS-357P catalloy, 4% by weight SUPER FLOSS diatomaceous earth made by McCullough and Benton, and 0.5% by weight B-900 antioxidant made by Ciba Specialties Company. The skin layers constituted about 3% of the total film thickness.

Example 2

The film of Example 2 was a single-layer film containing 48% by weight (74.2% by volume) of a polymer combination and 52% by weight (25.8% by volume) of the same calcium carbonate used in Example 1. The polymer combination contained 41.7% by weight Dow EG-8200, single-site catalyzed very low density polyethylene having a density of 0.87 grams/cm$^3$ and an octene comonomer, available from Dow Chemical Co. The polymer combination also contained 58.3% by weight Dowlex 2517, a Ziegler-Natta catalyzed linear low density polyethylene having a density of 0.917 grams/cm$^3$ and an octene comonomer, available from Dow Chemical Co.

Example 3

The film of Example 3 was a single-layer film containing 48% by weight (74% by volume) of a polymer combination and 52% by weight (26% by volume) of the same calcium carbonate used in Example 1. The polymer combination contained 20.3% by weight Dow EG-8200 and 79.7% by weight Dowlex 2517.

For the experiments set forth below, the test film and laminate samples were prepared as follows. Adhesive is applied to one face of a Mocon metal sample holder. The sample holder holds six specimens. The adhesive was applied using a 3M adhesive transfer tape but double-faced sticky tape or equivalent would also be acceptable. A piece of the test material put in a mechanical stretcher. The mechanical stretcher has twelve-inch long jaws that were separated by 20.3 cm (8 inches). The piece of test material was put into the mechanical stretcher and elongated 25%, i.e., the jaw separation was increased from 20.3 cm (8 inches) to 25.4 cm (10 inches). The sample holder was pressed against the test material to adhesively attach the stretched material to the sample holder. The material piece was cut appropriately to allow for the sample holder to be put into the Mocon unit. It is very important to ensure that the adhesive being used is strong enough to stop the sample from separating from the sample holder and retracting.

In a first set of experiments, the film of Examples 2 and 3 were a) tested for WVTR and hydrohead resistance, then b) stretched by 25% in the cross-direction at room temperature, then c) tested again for WVTR and hydrohead resistance. Table 1 gives the results.

thickness of 1.8–1.9 mils. Each cast film was stretch oriented to about five times its original length in the machine direction (MD), using a stretching temperature of about 155° C. The stretched films were annealed at 210° C. Some of the MD stretched films were laminated to a polypropylene spunbond web having a basis weight of about 14 grams per square meter (gsm), and a fiber denier of 2.0–2.5 dpf. The lamination was accomplished by using a meltblowing applicator to deposit 2–5 gsm of Findley 2525A hot melt adhesive to the spunbond web, and then lightly passing the film and spunbond web together between a pair of nip rollers.

MD-stretched films, and laminates including the MD-stretched films, were extended in the cross direction (CD) by about 25%, to about 125% of their width prior to CD stretching, using the method described in Example 3. The force required to extend the films and laminates in the cross direction was measured according to ASTM Procedure D-5035, modified in that a 3-inch wide sample was used instead of a 2-inch wide sample, and strain was recorded at 25% cross-directional elongation. The WVTR of the films and laminates were measured before and after the CD stretching.

TABLE 1

Evaluation of Film Samples

| | WVTR, grams/m²-24 hours | | Hydrohead, mbar | | | |
| --- | --- | --- | --- | --- | --- | --- |
| | | | Before CD Stretch | | After CD Stretch | |
| Example No. | Before CD Stretch | After CD Stretch | Supported | Unsupported | Supported | Unsupported |
| 2 | 500 | 12,000 | 166 | 42 | 159 | 51 |
| 3 | 17,000 | 64,000 | 165 | 68 | 165 | 65 |

As shown above, the minimal cross-directional stretch greatly improved the WVTR, and had little effect on hydrohead resistance.

In a second set of experiments, the films of Examples 1–3 were adhesively laminated to a 33% necked polypropylene spunbond web using 3 grams/square meter of Ato Findley 2525A meltblown adhesive. The laminates were a) tested for WVTR, then b) stretched at room temperature by 25% in the cross-direction, then c) tested again for WVTR. Table 2 gives the results.

TABLE 2

Evaluation of Laminate Samples

| | WVTR, grams/m²-24 Hours | |
| --- | --- | --- |
| Example No. | Before CD Stretch | After CD Stretch |
| 1 | 16,000 | 32,000 |
| 2 | 800 | 7,000 |
| 3 | 19,000 | 37,000 |

As shown above, the laminate made from the film of Example 2 gave the best combination of low WVTR before cross-directional stretching, and much higher WVTR after cross-directional stretching.

Examples 4–7

The following Examples further illustrate the performance of various films of the invention, and of film/nonwoven laminates containing the films. Each film was prepared on a pilot cast extrusion line, and had an initial width (prior to stretching) of about 20 inches and an initial The films had the following compositions.

Example 4

The film of Example 4 was a single-layer film containing 47.5% by weight (73.4% by volume) of a polymer combination and 52.5% by weight (26.6% by volume) of the same calcium carbonate used in Example 1. The polymer combination contained 35.8% by weight Dow ENGAGE EG-8200 (single-site catalyzed, very low density polyethylene having a density of 0.87 g/cm³ and an octene comonomer), 63.8% by weight Dowlex 2517 (Ziegler-Natta catalyzed linear low density polyethylene having a density of 0.917 g/cm³ and an octene comonomer), and 0.4% by weight Ciba B900 antioxidant from Ciba-Geigy Co.

Example 5

The film of Example 5 was a three-layer coextruded film containing a core layer and two skin layers. The core layer contained 44% by weight (29.5% by volume) of a polymer combination and 56% by weight (70.5% by volume) of the same calcium carbonate used in Example 1. The polymer combination contained 34.1% by weight Dow ENGAGE EG-8200 (single-site catalyzed, very low density polyethylene having a density of 0.87 g/cm³ and an octene comonomer), 65.5% by weight Huntsman 3106 (Ziegler-Natta catalyzed, linear low density polyethylene having a density of 0.919 g/cm³ and an octene comonomer, available from Huntsman Chemical Co.), and 0.4% by weight Ciba 900 antioxidant. The core layer constituted 98% of the total film thickness.

Each skin layer was composed of Exxon-Mobil LQA-006 (Ziegler-Natta catalyzed, branched low density polyethylene having a density of 0.918 grams/cc, available from Exxon- Mobil Chemical Co.). Each skin layer constituted 1.0% of the total film thickness.

Example 6

The film of Example 6 was a three-layer coextruded film identical to the film of Example 5 except that the Huntsman 3106 in the core layer was replaced with an equal amount of Dow NG3310 (Ziegler-Natta catalyzed, linear low density polyethylene having a density of 0.917 g/cm$^3$ and an octene comonomer, available from Dow Chemical Co.). The remaining components, amounts and layer thicknesses were the same as in the film of Example 5.

Example 7

The film of Example 7 was a three-layer coextruded film having the same core layer composition as the film of Example 6. The core layer constituted 97% of the total film thickness.

Each skin layer contained 50.4% by weight Montell KS357P catalloy (a heterophasic polymer containing i) 50% propylene-ethylene random copolymer containing 4% ethylene and 96% propylene, all by weight, ii) 5% ethylene-propylene copolymer containing 60% ethylene, essentially in blocks, and 40% propylene, and iii) 45% propylene-ethylene random copolymer containing 20% ethylene and 80% propylene), 22.5% by weight Exxon-Mobil LD755.12 (ethylene vinyl acetate having a density of 0.951 g/cc and containing 28% vinyl acetate), 22.5% by weight Exxon-Mobil LD761 (ethylene vinyl acetate having a density of 0.950 g/cc and containing 28% vinyl acetate), 4% by weight diatomaceous earth, and 0.6% by weight Ciba 900 antioxidant. Each skin layer constituted 1.5% of the total film thickness.

Tables 3 and 4 indicate the breathability before and after the 25% CD stretching, and the stretching force required, for the films and laminates of Examples 4–7. Table 3 provides the evaluation results for the films, while Table 4 provides the evaluation results for the laminates.

TABLE 3

Evaluation of Film Samples

WVTR, grams/m$^2$-24 hours

| Example No. | Before CD Stretch | After CD Stretch | Stretching Force, grams |
|---|---|---|---|
| 4 | 8,000 | Not Available | 325–350 |
| 5 | 14,000 | 40,200 | 325–350 |
| 6 | 11,000 | 24,800 | 325–350 |
| 7 | 11,000 | 33,900 | 325–350 |

TABLE 4

Evaluation of Laminate Samples

WVTR, grams/m$^2$-24 hours

| Example No. | Before CD Stretch | After CD Stretch | Stretching Force, grams* |
|---|---|---|---|
| 4 | Not Available | Not Available | 325–350 |
| 5 | 12,040 | 27,993 | 325–350 |
| 6 | 8,618 | 22,911 | 325–350 |
| 7 | 7,844 | 22,260 | 325–350 |

*estimated based on the stretching force of the films, which essentially controls the stretching force of the laminates at low levels of cross-directional extension.

As shown above, the films and laminates of Examples 4–7 had low cross-directional stretching force as could be easily applied by a user during installation of a garment containing the films and/or laminates. The CD-stretched films and laminates also had excellent breathability to water vapor, and excellent improvement in breathability compared to the unstretched films and laminates.

While the embodiments of the invention disclosed herein are presently considered preferred, various modifications and improvements can be made without departing from the spirit and scope of the invention. The scope of the invention is indicated by the appended claims, and all changes that fall within the meaning and range of equivalents are intended to be embraced therein.

We claim:

1. A substantially liquid-impermeable film that is extendible in a cross-direction to a stretched width that is at least 25% greater than an unstretched width upon application of a stretching force;
   the film comprising at least one layer which includes a single-site catalyzed olefin polymer, a Ziegler-Natta catalyzed olefin polymer, and a particulate filler;
   the film having a first water vapor transmission rate of at least about 500 grams/m$^2$-24 hours at the unstretched width;
   the film having a second water vapor transmission rate which is at least 225% of the first water vapor transmission rate and not less than about 4000 grams/m$^2$-24 hours, at a stretched width that is 25% greater than the unstretched width.

2. The film of claim 1, wherein the second water vapor transmission rate is at least 250% of the first water vapor transmission rate.

3. The film of claim 1, wherein the second water vapor transmission rate is at least 300% of the first water vapor transmission rate.

4. The film of claim 1, wherein the second water vapor transmission rate is at least about 5500 grams/m$^2$-24 hours.

5. The film of claim 1, wherein the second water vapor transmission rate is at least about 7000 grams/m$^2$-24 hours.

6. The film of claim 1, having a stretched length in a machine direction that is 1.1–7.0 times an original, unstretched length, wherein the first water vapor transmission rate exists at the stretched length.

7. The film of claim 6, wherein the stretched length is 1.5–6.0 times the unstretched length.

8. The film of claim 6, wherein the stretched length is 2.5–5.0 times the unstretched length.

9. The film of claim 1, further comprising at least one skin layer.

10. The film of claim 1, wherein the layer includes about 10–55% by volume of the filler and about 45–90% by volume of total polymer, the total polymer including about 10–90% by weight of the single-site catalyzed olefin polymer and about 10–90% by weight of the Ziegler-Natta catalyzed olefin polymer.

11. The film of claim 10, wherein the layer includes about 15–45% by volume of the filler and about 55–85% by volume of total polymer.

12. The film of claim 10, wherein the layer includes about 25–40% by volume particulate filler and about 60–75% by volume of total polymers.

13. The film of claim 10, wherein the total polymer includes about 25–75% by weight of the single-site catalyzed olefin polymer and about 25–75% by weight of the Ziegler-Natta catalyzed olefin polymer.

14. The film of claim 10, wherein the total polymer includes about 30–60% by weight of the single-site catalyzed olefin polymer and about 40–70% by weight of the Ziegler-Natta catalyzed olefin polymer.

15. The film of claim 1, wherein the single-site catalyzed olefin polymer has a lower density and the Ziegler-Natta catalyzed olefin polymer has a higher density.

16. The film of claim 1, wherein the single-site catalyzed olefin polymer has a density of 0.870 grams/cm$^3$ to less than 0.900 grams/cm$^3$ and the Ziegler-Natta catalyzed olefin polymer has a density of about 0.900–0.935 grams/cm$^3$.

17. A substantially liquid-impermeable breathable film that is extendible in a cross direction to a stretched width that is at least 25% greater than an unstretched width upon application of a stretching force;

the film comprising a filled layer which includes about 10–55% by volume of a particulate filler and about 45–90% by volume of total polymer;

the total polymer including about 10–50% by weight of a single-site catalyzed very low density polyethylene and about 50–90% by weight of a Ziegler-Natta catalyzed linear low density polyethylene;

the film having a first water vapor transmission rate of at least about 500 grams/m$^2$-24 hours at the unstretched width and a second water vapor transmission rate which is at least about 4000 grams/m$^2$-24 hours at a stretched width that is 25% greater than the unstretched width.

18. The film of claim 17, wherein the filled layer comprises about 15–45% by volume of the filler and about 55–85% by volume of the total polymer.

19. The film of claim 17, wherein the filled layer comprises about 25–40% by volume of the filler and about 60–75% by volume of the total polymer.

20. The film of claim 17, wherein the total polymer comprises about 25–50% by weight of the very low density polyethylene and about 50–75% by weight of the linear low density polyethylene.

21. The film of claim 17, further comprising at least one skin layer.

22. The film of claim 17, wherein the second water vapor transmission rate is at least 225% of the first water vapor transmission rate.

23. A substantially liquid-impermeable film that is extendible in a cross direction to a stretched width that is at least 25% greater than an unstretched width upon application of a stretching force;

the film comprising a filled layer which includes a lower density olefin polymer having a density of 0.870 grams/cm$^3$ to less than 0.900 grams/cm$^3$, a higher density olefin polymer having a density of 0.900–0.935 grams/cm$^3$, and a particulate filler;

the film having a first water vapor transmission rate of at least 500 grams/m$^2$-24 hours at the unstretched width and a second water vapor transmission rate at least 225% of the first water vapor transmission rate and at least 4000 grams/m$^2$-24 hours at the stretched width.

24. The film of claim 23, wherein the lower density olefin polymer comprises a single-site catalyzed polymer.

25. The film of claim 24, wherein the higher density olefin polymer comprises a Ziegler-Natta catalyzed olefin polymer.

26. The film of claim 23, wherein the second water vapor transmission rate is at least 250% of the first water vapor transmission rate.

27. The film of claim 23, wherein the second water vapor transmission rate is at least 300% of the first water vapor transmission rate.

28. The film of claim 23, wherein the filled layer comprises about 10–55% by volume of the filler and about 45–90% by volume of total polymer, the total polymer including the lower density olefin polymer and the higher density olefin polymer.

29. The film of claim 28, wherein the total polymer includes about 25–75% by weight of the lower density olefin polymer and about 25–75% by weight of the higher density olefin polymer.

30. The film of claim 28, wherein the total polymer includes about 30–60% by weight of the lower density olefin polymer and about 40–70% by weight of the higher density olefin polymer.

* * * * *

UNITED STATES PATENT AND TRADEMARK OFFICE
CERTIFICATE OF CORRECTION

PATENT NO. : 6,811,865 B2
DATED : November 2, 2004
INVENTOR(S) : Michael Tod Morman et al.

It is certified that error appears in the above-identified patent and that said Letters Patent is hereby corrected as shown below:

Column 15,
Line 44, change "$Fp_{sat}(T)RH/Ap_{sat}(T)(1-RH))$" to -- $F\rho_{sat}(T)RH/A\rho_{sat}(T)(1-RH)$ -- and
Line 48, change "$p_{sat}(T)$" to -- $\rho_{sat}(T)$ --.

Signed and Sealed this

First Day of March, 2005

JON W. DUDAS
*Director of the United States Patent and Trademark Office*